United States Patent [19]

Lachhein et al.

[11] Patent Number: 5,070,201

[45] Date of Patent: Dec. 3, 1991

[54] PROCESS FOR THE PREPARATION OF AMINOPYRIMIDINES

[75] Inventors: Stephen Lachhein, Hofheim am Taunus; Lothar Willms, Hillscheid, both of Fed. Rep. of Germany

[73] Assignee: Hoechst AG, Frankfurt am Main, Fed. Rep. of Germany

[21] Appl. No.: 601,224

[22] Filed: Oct. 22, 1990

[30] Foreign Application Priority Data

Oct. 24, 1989 [DE] Fed. Rep. of Germany ....... 3935278

[51] Int. Cl.⁵ .............................................. C07D 239/42
[52] U.S. Cl. ..................................................... 544/320
[58] Field of Search ......................................... 544/320

[56] References Cited

U.S. PATENT DOCUMENTS 4,169,719 10/1979 Levitt ........................................ 71/92
4,492,598 1/1985 Willms et al. ............................ 71/93

FOREIGN PATENT DOCUMENTS 0024200 2/1981 European Pat. Off. .
0071958 2/1983 European Pat. Off. .
2426913 12/1975 Fed. Rep. of Germany .

*Primary Examiner*—John M. Ford
*Attorney, Agent, or Firm*—Curtis, Morris & Safford

[57] ABSTRACT

Aminopyrimidines of the formula (I)

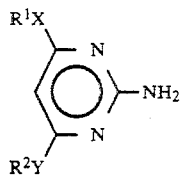

in which
X and Y are in each case oxygen or sulfur and
$R^1$, $R^2$ are independently of one another ($C_1$–$C_4$)alkyl, ($C_1$–$C_4$)alkoxy-($C_1$–$C_2$)alkyl or halo($C_1$–$C_4$)alkyl, are intermediates for the preparation of herbicides from the sulfonylurea group. According to the invention, compounds of the formula I can be prepared in a one-step process without pH control, which comprises the reaction of a propanediimidate of the formula

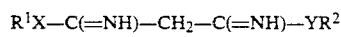

or its salt with an alkali metal or alkaline earth metal salt of the cyanamide, in which a solution of the compounds in an alcohol of the formula $R^4$—OH, in which $R^4$ is ($C_1$–$C_6$)alkyl, or, simultaneously, separate solutions of the compounds in each case in an alcohol $R^4$—OH are added to an inert organic solvent which is higher-boiling in comparison to the alcohol at temperatures above 100° C. with simultaneous removal of the alcohol by distillation.

9 Claims, No Drawings

PROCESS FOR THE PREPARATION OF AMINOPYRIMIDINES

DESCRIPTION

The invention relates to a process for the preparation of pyrimidines of the formula I

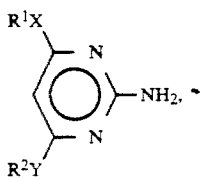   I in which
X and Y are in each case oxygen or sulfur and
$R^1$, $R^2$ are independently of one another $(C_1-C_4)$alkyl, $(C_1-C_4)$alkoxy-$(C_1-C_2)$alkyl or halo$(C_1-C_4)$alkyl,
which comprises reacting a propanediimidate of the formula II

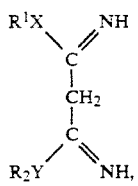   II or its salt, where $R^1$, $R^2$, X and Y have the meaning defined for formula I, with a salt of the cyanamide of the formula III

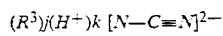   III, in which
$R^3$ is an alkali metal or alkaline earth metal cation and
j=1 and k=0 if $R^3$ is an alkaline earth metal cation or
j=1 and k=1 or
j=2 and k=0 if $R^3$ is an alkali metal cation,
in which a solution of the compounds of the formulae II and III in an alcohol of the formula IV

   IV, in which $R^4$ is $(C_1-C_6)$alkyl, or, simultaneously, separate solutions of the compounds of the formulae II and III in each case in an alcohol of said formula IV are added to an inert organic solvent which is higher-boiling compared to the alcohol at temperatures above 100° C. with simultaneous removal of the alcohol of the formula IV by distillation.

The compounds of the formula I are useful intermediates for the preparation of sulfonylureas having herbicidal action. See, for example, U.S. Pat. No. 4,169,719 or EP 071,958 (U.S. Pat. No. 4,492,598).

In the radicals $R^1$ and $R^2$, alkyl is methyl, ethyl, propyl, isopropyl or n-, i-, t- or 2-butyl. In the radical $R^4$, suitable radicals in addition to these are the straight-chain or branched pentyls or hexyls. Haloalkyl is alkyl substituted by fluorine, chlorine, bromine or iodine. Alkoxy is alkyl-oxy with the possible meanings mentioned in the alkyl moiety.

It is known that pyrimidines of the formula I can be prepared by reaction of propanediimidates with aqueous cyanamide solution or cyanogen chloride in a two- or three-step process (EP-A-0,024,200), the formation and subsequent isolation of an N-cyanoimidate as an intermediate being regarded as characteristic features of the process. However, the yields of the final product which can be obtained in this case are unsatisfactory. Other disadvantages of said process are: the formation of not inconsiderable amounts of by-products, the necessity of conducting the reaction within a narrow pH range and the additional use of a base. Moreover, it is disadvantageous that the inorganic salts formed during the reaction, specifically when employing aqueous cyanamide solution, pass into the waste water in dissolved form and must be removed therefrom by additional measures.

Surprisingly, in contrast, in terms of process engineering the process according to the invention is a simple one-step process without isolatable intermediates which permits conduct of the reaction without pH control. By-products are only formed to a minor extent.

In the process according to the invention, the strongly basic salts of the cyanamide attack the imidate structure. The high selectivity for the formation of compounds of the formula I and the high yields associated therewith were not to be expected owing to the strongly basic nature of the cyanamide salts and the structure of the propanediimidates which is sensitive to nucleophiles. Moreover, it is known that imidates or bisimidates are thermolabile, particularly in their salt form. It was therefore not to be expected that the propanediimidates would be so stable at the high reaction temperatures above 100° C. that high yields of, for example, 90 % and more could be obtained in the process according to the invention.

The reaction is carried out in a non-aqueous organic solvent which is inert under the reaction conditions, so that virtually no free cyanamide can be formed by hydrolysis. The inorganic salts formed during the reaction precipitate as solids which are filtered off and thus do not pass into the waste water. In addition to the process engineering and economical advantages already described, this aspect of the process is to be regarded as progressive from the ecological point of view. After completion of the reaction and removal of the solvent, which is nearly recovered quantitatively, by distillation, the reaction product remains in high purity.

The process according to the invention ca be carried out, for example, in such a way that the propanediimidate as the monosalt, disalt or as free bisimidate is dissolved in an alcohol, preferably at −10° C. to +10° C., together with a cyanamide salt of the formula III and the solution obtained is metered into the inert organic solvent above 100° C. Alternatively, for example, a solution of propanediimidate as the monosalt, disalt or as free bisimidate in an alcohol adjusted to −10° C. to +10° C. can be simultaneously metered into the inert organic solvent above 100° C. with a solution of a cyanamide salt of the formula II in an alcohol. During the continuous addition of the alcoholic solution or the alcoholic solutions, the alcohol is continuously removed from the reaction mixture by distillation.

In the reaction between the compounds of the formulae II and III, no intermediate compounds can be isolated or detected, but the pyrimidines of the formula I are formed directly.

Salts of the propanediimidate preferably employed are those of hydrofluoric, hydrochloric or hydrobromic acid, sulfuric acid or phosphoric acid. Haloalkyl radicals for $R^1$, $R^2$ are, for example, $CH_2CH_2Cl$ or $CH_2CF_3$. The preferred meaning of X, Y is oxygen and of $R^1$, $R^2$ ($C_1$-$C_4$)alkyl, in particular methyl.

The choice of the inert organic solvent depends on the boiling point of the alcohol. The alcohol must be allowed to distill off from the reaction mixture during the reaction. Solvents are, for example, aliphatic and optionally halogenated aromatic hydrocarbons, but also solvents from the ketone group, such as methyl isobutyl ketone, and other chemical classes.

Suitable alcohols are above all methanol and ethanol. Preferred inert organic solvents are aromatic hydrocarbons such as, for example, toluene, xylene or chlorobenzene.

In order to avoid interfering influences of oxygen on the reaction, it is expedient to work under an inert gas atmosphere, for example under nitrogen.

The compounds of the formula II can be prepared by known methods (S. M. McElvain and I. D. Schröder, JACS 71, 40 (1949); B. Harstun, DOS 2,426,913).

The following examples are intended to illustrate the process according to the invention in more detail:

Example 1

102 g of dimethylpropanediimidate hydrochloride and 33 g of monosodium cyanamide are dissolved in 1000 ml of methanol at 0° C. under a nitrogen blanket and added dropwise in the course of 2 hours to chlorobenzene at 120° C. During this time, the methanol is continuously removed by distillation and the product concentrates in the chlorobenzene phase. After completion of the reaction, the precipitated salt is filtered off and the chlorobenzene is removed by distillation. 69.3 g of 2-amino-4,6-dimethoxypyrimidine remain, which corresponds to a yield of 89 % of theory. The melting point is 92°–94° C. Analogous results are obtained using toluene or xylene as the inert solvent.

Example 2

102 g of dimethylpropanediimidate hydrochloride are dissolved in 500 ml of ethanol at +10° C. under nitrogen and simultaneously metered into a chlorobenzene solution at 120° C. with a solution of 43 g of disodium cyanamide in 500 ml of ethanol in the course of 3 hours. During this time, the ethanol is continuously distilled off. After completion of the reaction, precipitated salt is filtered off and the chlorobenzene is removed by distillation. 70.0 g of 2-amino-4,6-dimethoxypyrimidine remain, which corresponds to a yield of 90 % of theory. The melting point is 92°–93° C. Analogous results are obtained using toluene and xylene as the inert solvent.

The following compounds of the formula I are obtained, for example, in accordance with the procedures described in Examples 1 or 2:

| Example | X | Y | $R^1$ | $R^2$ |
|---|---|---|---|---|
| 3 | O | O | $C_2H_5$ | $C_2H_5$ |
| 4 | O | O | CH—CH$_3$<br>\|<br>CH$_3$ | CH—CH$_3$<br>\|<br>CH$_3$ |
| 5 | S | S | CH$_3$ | CH$_3$ |
| 6 | S | S | $C_2H_5$ | $C_2H_5$ |
| 7 | S | S | CH—CH$_3$<br>\|<br>CH$_3$ | CH—CH$_3$<br>\|<br>CH$_3$ |

We claim:

1. A process for the preparation of compounds of the formula I

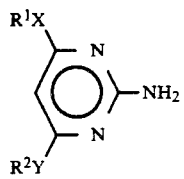

in which
X and Y are in each case oxygen or sulfur and
$R^1$, $R^2$ are independently of one another ($C_1$-$C_4$)alkyl, ($C_1$-$C_4$)alkoxy-($C_1$-$C_2$)alkyl or halo($C_1$-$C_4$)alkyl, which comprises reacting a propanediimidate of the formula II

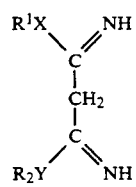

or its salt, where $R^1$, $R^2$, X and Y have the meaning defined for formula I, with a salt of the cyanamide of the formula III

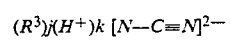

in which
$R^3$ is an alkali metal or alkaline earth metal cation and
j=1 and k=0 if $R^3$ is an alkaline earth metal cation or
j=1 and k=1 or
j=2 and k=0 if $R^3$ is an alkali metal cation, in which a solution of the compounds of the formulae II and III in an alcohol of the formula IV

in which
$R^4$ is ($C_1$-$C_6$)alkyl, or, simultaneously, separate solutions of the compounds of the formulae II and III in each case in an alcohol of said formula IV are added to an inert organic solvent which is higher-boiling compared to the alcohol at temperatures above 100° C. with simultaneous removal of the alcohol of the formula IV by distillation.

2. The process as claimed in claim 1, wherein, in formula I,
X and Y are in each case an oxygen atom and
$R^1$ and $R^2$ are ($C_1$-$C_4$)alkyl.

3. The process as claimed in claim 1, wherein, in formula I, $R^1$ and $R^2$ are in each case methyl or ethyl.

4. The process as claimed in claim 1, wherein salts of the compound of the formula II which are used are those of hydrofluoric, hydrochloric or hydrobromic acid, sulfuric acid or phosphoric acid.

5. The process as claimed in claim 1, wherein an optionally halogenated hydrocarbon is employed as the inert organic solvent.

6. The process as claimed in claim 5, wherein chlorobenzene, toluene or xylene is employed.

7. The process as claimed in claim 1, wherein the alcohol of the formula IV is methanol or ethanol.

8. The process as claimed in claim 1, wherein the solution or the solutions of the compounds of the formula II or III in the alcohol of the formula IV are adjusted to $-10°$ to $+10°$ C.

9. The process as claimed in claim 1, wherein precipitated inorganic salts are filtered off from the reaction solution after the reaction and the inert organic solvent is removed by distillation.

* * * * *